United States Patent [19]

Rivola et al.

[11] Patent Number: 5,241,301
[45] Date of Patent: Aug. 31, 1993

[54] DEVICE AND METHOD FOR REAL-TIME MONITORING OF ACCIDENTAL DAMAGE TO THE PROTECTIVE COVERING OF UNDERGROUND OR IMMERSED METAL STRUCTURES OR PIPELINES

[75] Inventors: Luigi Rivola, San Donato Milanese; Sebastiano Di Liberto, San Giuliano Milanese, both of Italy

[73] Assignee: ENIRICERCHE S.p.A., Milan, Italy

[21] Appl. No.: 805,855

[22] Filed: Dec. 10, 1991

[30] Foreign Application Priority Data

Dec. 14, 1990 [IT] Italy ................................ 22395 A/90

[51] Int. Cl.$^5$ ............................................. G08B 21/00
[52] U.S. Cl. ..................................... 340/660; 340/659; 340/635; 204/147; 204/196
[58] Field of Search ............... 340/660, 661, 659, 635, 340/664; 204/147, 196; 361/88, 90, 91, 92; 324/76 R, 133

[56] References Cited

U.S. PATENT DOCUMENTS 4,255,242 3/1981 Freeman ............................ 204/147

FOREIGN PATENT DOCUMENTS 0148267 7/1985 European Pat. Off. .
0411689 2/1991 European Pat. Off. .

Primary Examiner—Jin F. Ng
Assistant Examiner—Jeffrey A Hofsass
Attorney, Agent, or Firm—Robert D. Schaffer

[57] ABSTRACT

A method for monitoring damage to the protective covering of immersed or underground metal structures subjected to cathodic protection, based on the electrical resistance offered by said covering, and consisting of modulating the cathodic protection feed current and measuring the corresponding potential variation due to the ohmic loss, said resistance being obtained from the ratio of potential variation to modulation current, to activate an alarm system on sudden fall and rise in ohmic resistance due to accidental events.

8 Claims, 4 Drawing Sheets

DEVICE AND METHOD FOR REAL-TIME MONITORING OF ACCIDENTAL DAMAGE TO THE PROTECTIVE COVERING OF UNDERGROUND OR IMMERSED METAL STRUCTURES OR PIPELINES

BACKGROUND OF THE INVENTION

1. Field of the Invention

This invention relates to the protection of underground or immersed structures exposed to wet corrosion.

In industrial practice many metal structures suffer from this technical problem, for example underground fuel storage tanks, off-shore structures, fluid transporting pipelines such as water, gas and oil pipelines, and other infrastructures for industrial, civil or military use.

The present invention is described with reference to underground pipelines, this constituting one of its most difficult and interesting applications, but without in any way limiting it to this specific application.

2. Description of the Prior Art

Liquid or gas transporting pipelines, such as gas, water or oil pipelines, are formed by welding together lengths of metal pipe, generally of steel, the continuous pipeline assembled in this manner being laid in its final seat, generally consisting of a sufficiently deep trench, and then covered in order to recreate the pre-existing environment and hence not hinder its further use. The assembled continuous pipeline is provided with protection against wet corrosion, as the environment in which the underground or immersed pipeline lies is very aggressive towards ferrous materials.

The integrity and preservation of the pipeline during its entire operating life are very important not only because of its high construction cost but also, and in particular, because fluid leakages must be prevented both because of their economical aspect and because they must not be allowed to cause danger, pollution or serious disturbance. The protection generally used consists of two different types of protection in mutual cooperation, namely "passive" protection consisting of a covering which isolates the pipeline from the surrounding environment and "cathodic" protection which applies an electric potential for inhibiting possible electrochemical reactions which could attack the pipeline metal to the extent of forming a through hole.

The "passive" protection is generally formed by applying a continuous covering to the properly cleaned pipeline. This covering can be of two main types, the first type being coverings of hydrocarbon materials such as asphalts, bitumens and fats which are generally applied hot in a number of layers together with fibrous material reinforcements, and the second type being synthetic polymer coverings such as polyethylene, polyvinylchloride and epoxy polymers, these being applied in the form of strips wound spirally about the pipeline and superimposing the side edges, or by diecasting. Web, felt or card made of glass wool, asbestos or other non-rotting fibrous material are used as protection and reinforcement.

This protection is not on its own sufficient to protect an underground or water-immersed pipeline for the required time. In this respect, the following should be noted:

no material is free of a certain porosity and permeability, even if perfectly applied, and hence a certain passage of the chemical species responsible for corrosive attack takes place in any event through the protective layer, even if very slight;

the sequence of operations involved in the preparation, covering, lifting, laying and burying of the pipeline can result in immediate slight damage or imperfections to the applied covering, these defects then triggering corrosion phenomena;

the hydrocarbon or polymer materials and their reinforcements have a chemical stability which is very high but is not absolute, particularly in relation to temperature or humidity changes;

natural phenomena, such as earthquakes, landslips or floods, and accidental events can damage the pipeline passive protection.

The "cathodic" protection protects the pipeline at those points in which porosity, damage or imperfect application of the covering have left the metal surface exposed to corrosive attack.

The variation in the state of the passive protection covering on the pipeline can be monitored by the method described in European patent application Publ. No. 0,411,689 and U.S. patent application Ser. No. 07/557,968 now abandoned in the name of the present applicant.

According to this method, the cathodic protection current applied to the pipeline is modulated by square waves. The application of square waves signals enables the resistive components and the capacitive components constituting the overall impedance of the pipeline-earth system to be separated and determined.

The variation in the ohmic resistance of an underground pipeline, deriving from progressive ageing of the covering, from distributed microcorrosion and from variations in earth conductivity, shows a continuous pattern of fall-off to lower values. The effects produced by landslip follow the same pattern.

This method is aimed at monitoring the state of the covering but 7ithout involving repair, the most that can be done being to increase the cathodic protection using greater intensity currents to compensate the progressive reduction in impedance.

Instead, the present invention monitors accidental events which can damage the pipeline or rather its protective covering, for example in the case of underground pipelines any accidental impact by excavation equipment, which would cause a sudden deterioration concentrated within a section of the pipeline.

In the case of pipelines immersed in water, such accidents can be caused by anchors or anchoring chains, fishing equipment which trawls the water bed, watercraft which run aground in shallow water, dragging equipment etc.

In contrast to normal covering decay, this sudden concentrated damage requires urgent local repair, otherwise it could cause rapid decay of the entire pipeline.

From the variation in the ohmic loss RI of the pipeline shown in FIG. 1 it can be seen that if the cathodic current applied to the pipeline is permanently modulated (in accordance with diagram A) symmetrically about the desired current by means of square waves, the wave form of the voltage induced in the pipeline-earth system comprises rounded crests and cavities for the capacitive components and a vertical level difference RI for the ohmic components, reflecting the state of the pipeline covering. According to the cited European Patent Appln. 0,411,689 the state of the covering is monitored by using cathodic protection currents at low modulation level and in any event below 10%, the preferred modulation range being between 0.5% and 5%. The modulation frequency is less than 100 Hz, the preferred range being between 0.05 and 1.0 Hz, and the ratio of the two half-periods is between 0.001 and 1000, the preferred range being between 0.1 and 10.

The insulation resistance (R) offered by the covering is determined according to the cited patent application by measuring with a recording voltmeter the variation in the potential due to the ohmic loss ($\Delta V^*$), in accordance with diagram B, corresponding to the applied modulating current ($I^*$), where $I^*$ is the difference between the currents $I_{max}$ and $I_{min}$. Then:

$$R = \Delta V^*/I^*$$

This enables the insulation resistance R of the pipeline covering to be determined, this being a measurement of its integrity. Knowing the value of R, the effective protection potential ($V_p$) can be calculated once its apparent overall potential ($V_a$) and the total cathodic protection current (I) are known, using the formula:

$$V_p = V_a - RI$$

In the diagram of FIG. 1, the variation in the phenomenon shown on the left side of the diagram corresponds, as described up to this point, to the "natural" decay of the covering of the pipeline monitored by the monitoring system of European Patent Appln. 0,411,689.

In the absence of accidental events, this natural decay results in a slow continuous reduction in the value of RI.

The central part of the diagram of FIG. 1 shows the variation arising on accidental contact between a metal body and the metal part of the pipeline. It can be seen that the value of RI suddenly falls, whereas the wave crests and depressions, which correspond to the capacitive components, show substantially no modification. This pattern reflects the fact that the metal body which makes contact with the metal part of the pipeline acts as a conductor to earth.

The right side of the diagram of FIG. 1 shows the variation in the phenomenon when contact between the metal body and the pipeline ceases. It can be seen that the value of RI suddenly rises, but to a value of less than that prior to contact. This variation reflects the fact that the metal body no longer acts as a conductor, but that it has damaged the covering to a certain extent.

This accidental event therefore produces a phenomenon which is not typical of natural covering decay, namely a sudden fall in the ohmic resistance followed by a rise to a value dependent on the area of the damage.

SUMMARY OF THE INVENTION

The method and device of the present invention measure the voltage signal shown in diagram C of FIG. 1, and in particular the sudden fall and rise in the value of RI.

Graph A depicts the applied cathodic current symmetrically modulated about a desired current in the pipeline.

Graph B depicts the resultant voltage wave form in the pipeline.

Graph C depicts the decay of the insulation resistance (ohmic loss) of the covering of the pipeline as a further of the contact of the metal body to the pipeline.

Figure 2:
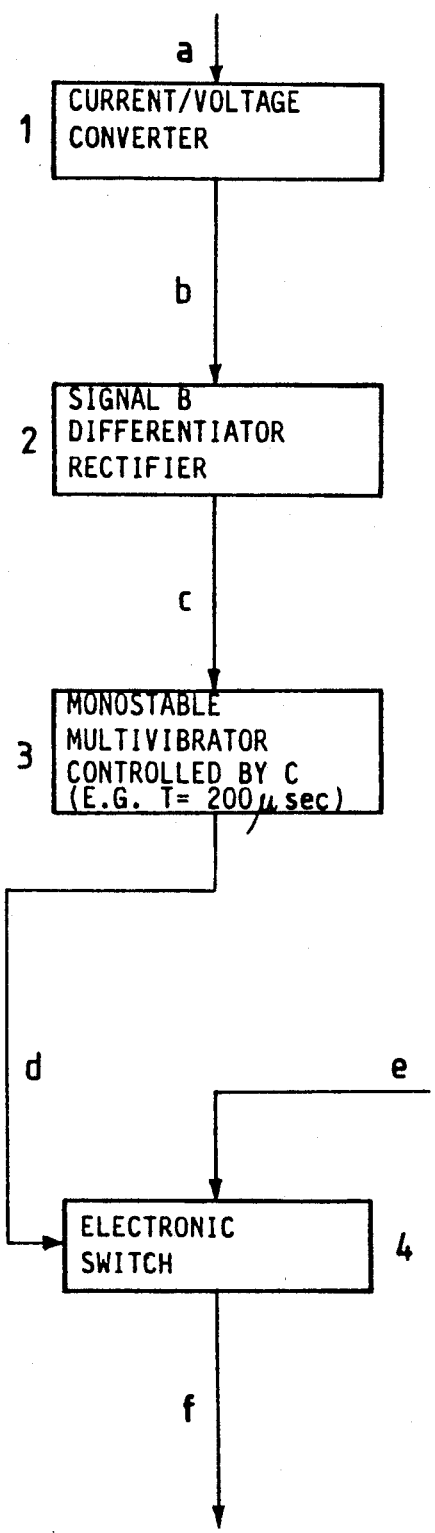
Figure 2:
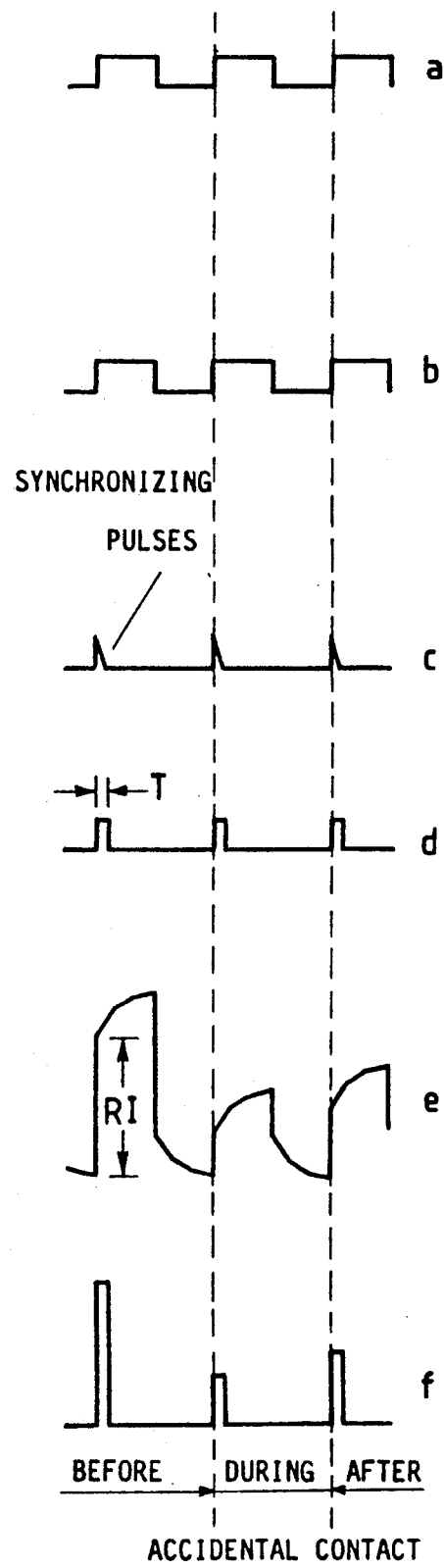

FIG. 2 illustrates a circuit, according to an embodiment of the present invention, for sampling the square wave signal.

Figure 1:
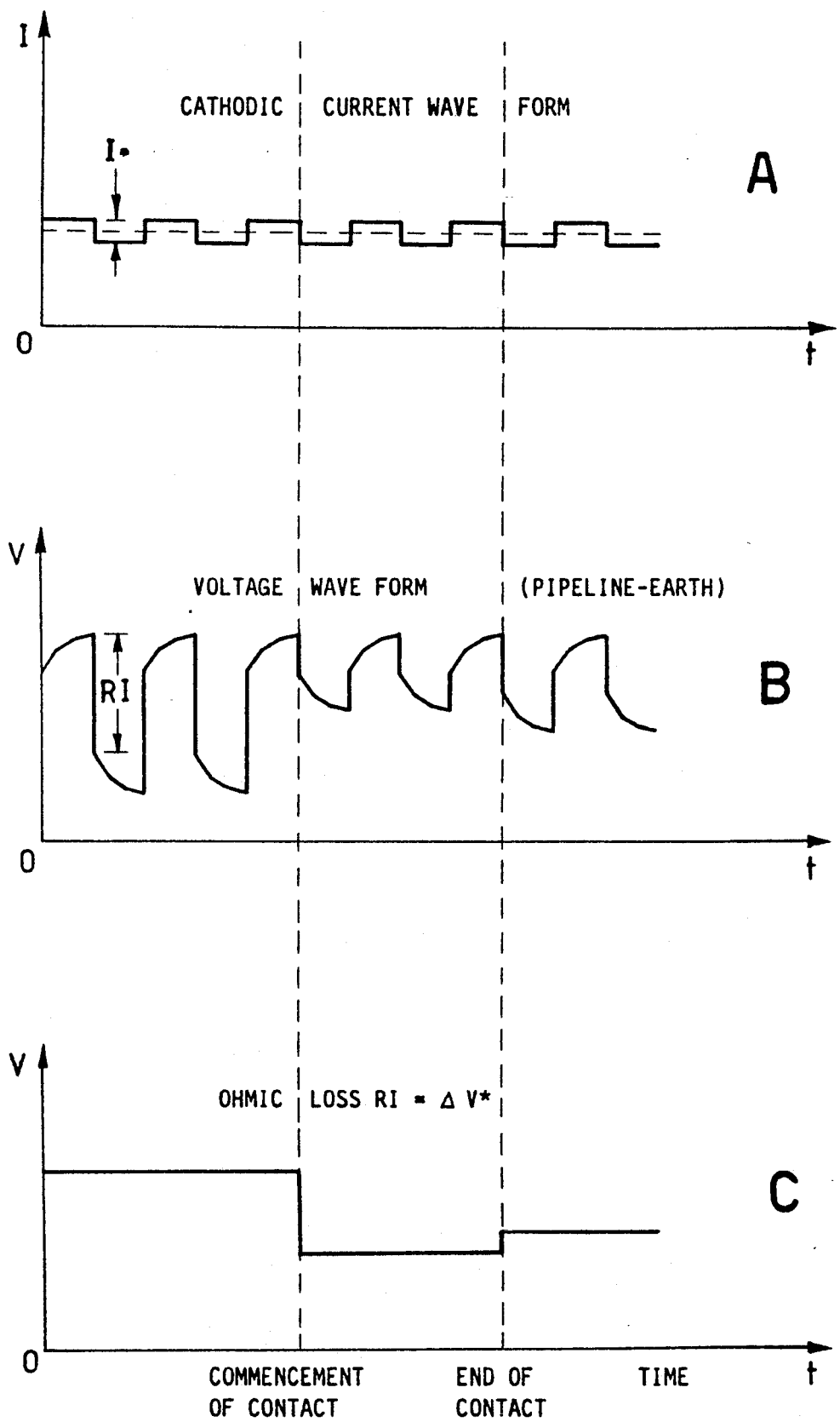
FIG. 1 illustrates three graphs labelled A, B, and C showing the result of the commencement of contact and the end of contact of a metal body to a pipeline.
Figure 3:
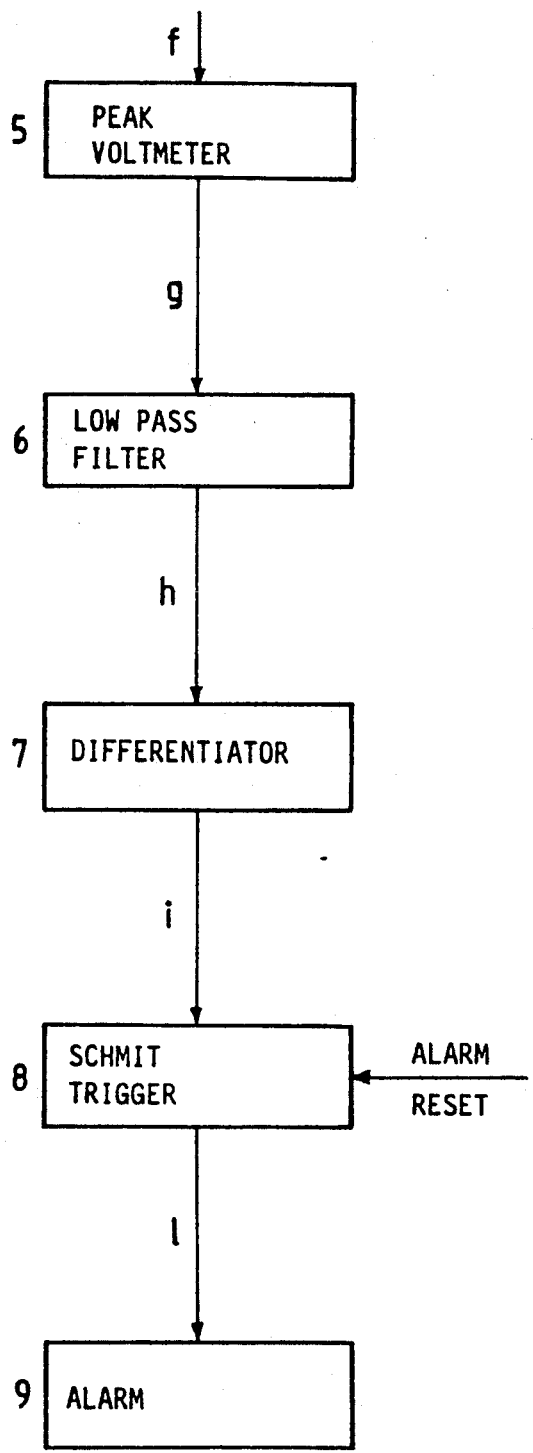
Figure 3:
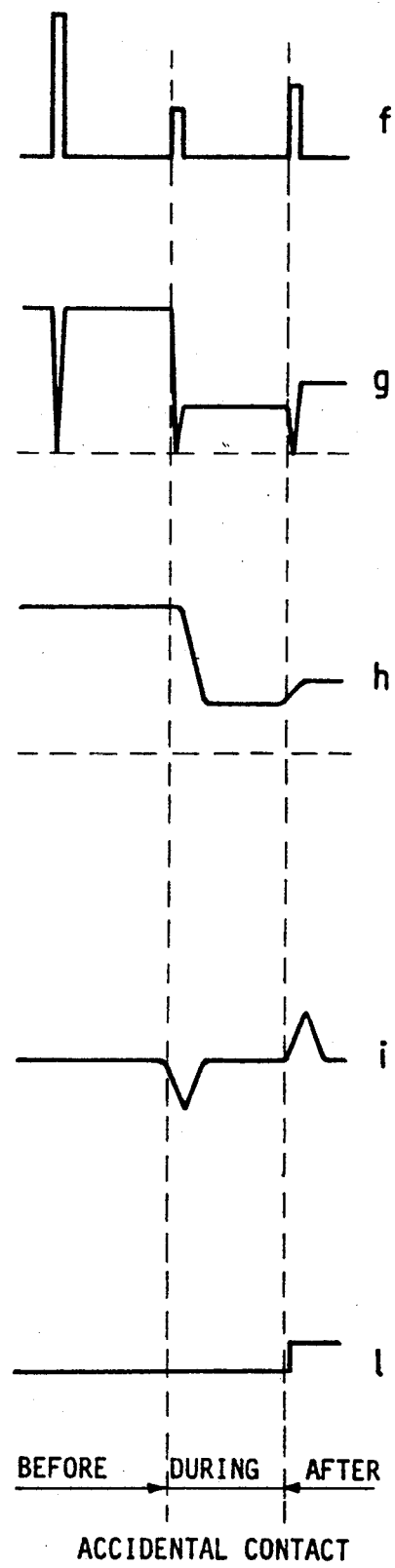

FIG. 3 illustrates a circuit, according to an embodiment of the present invention, for measuring the variation in the ohmic loss illustrated in FIG. 1.

Figure 4:
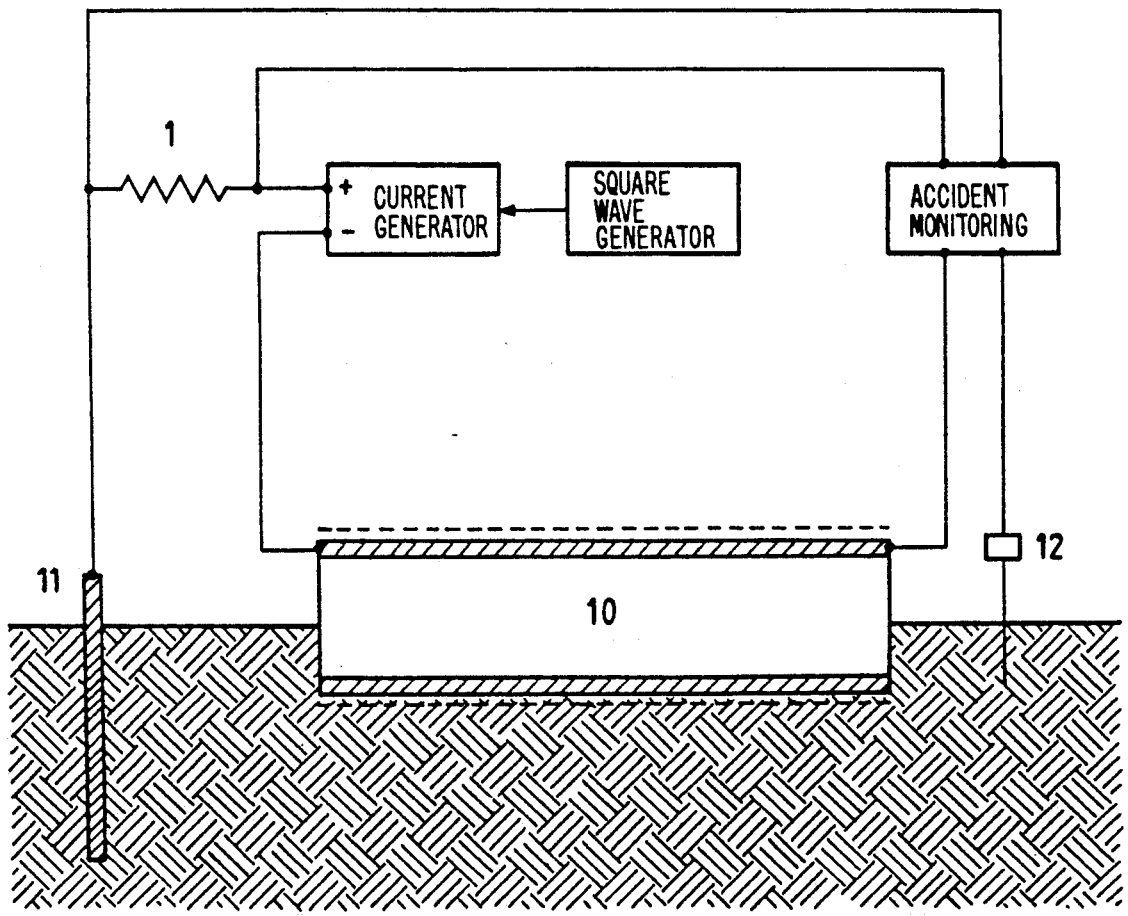

FIG. 4 illustrates a schematic view of an embodiment of the present invention.

DESCRIPTION OF THE PREFERRED EMBODIMENT

The device and method of the present invention are described by way of non-limiting example with reference to a typical embodiment shown in FIG. 2, which represents the circuit for sampling the square wave signal, and on FIG. 3, which represents the circuit for measuring the variation in the RI response signal in accordance with the pattern shown in FIG. 1.

The components of these circuits can be commercially available integrated circuits.

The block diagram on the left of FIG. 2, which on the right shows the shape of the correspondingly generated signal against time, comprises the following components:

a voltage/current converter (1) receiving a signal (a) corresponding to the square wave current fed to the pipeline for its cathodic protection, and consisting of a non-inductive resistor, which generates a signal (b), a differentiator/rectifier (2) which differentiates the signal (b) to generate positive and negative pulses at the wavefronts of (b); the rectifier included in (2) eliminates the negative peaks while preserving only the peaks relative to the rising wavefronts of (b) and generating synchronization pulses (c), a monostable multivibrator (3) controlled by the signal (c) to generate a square wave signal (d) of duration T, for example 200 microseconds, an electronic switch (4), for example a MOSFET analog switch, which allows the voltage signal (e) taken between the pipeline and a reference electrode inserted in the ground to pass only at the peaks of the signal (d), to generate as output a signal (f) with an amplitude directly related to the ohmic resistance of the pipeline, having eliminated the reactive and polarization components.

The block diagram on the left of FIG. 3, which on the right shows the shape of the correspondingly generated signal, comprises the following components:

a peak voltmeter (5) reset by the synchronization pulses (c), to measure the peak value of the signal (f) and provide the signal (g), a low-pass electronic filter (6) with a suitable time constant, to average the signal (g) in time and eliminate its steep wavefronts corresponding to the signal (c), and to provide the signal (h), a differentiator (7) with a suitable time constant (such as a few seconds) to determine the sudden increase in the ohmic resistance, deducible from the signal (h), and generate the signal (i), a blocked Schmitt trigger (8) which is activated by the rapid upward variation in the signal (i) in correspondence with the positive derivative of (h), to generate the damage signal (1); this signal can be of acoustic, luminous or other type, and remains active until (8) is reset.

EXAMPLE

A test pipeline is simulated by an 8" steel pipe of length 10 meters covered with polyethylene filled with carbon black, as normally used for methane pipelines. Some simulated defects with the metal surfaces directly in contact with the ground are introduced into the surface of the covering.

This pipe is partly buried and a constant current cathodic protection at a potential of between 1.0 and 1.5 V is applied to it, the direct current feed (1.5 mA/m$^2$) being modulated with square waves at a modulation depth of between 1 and 5% and a frequency of between 0.5 and 10 Hz, in accordance with the scheme /f FIG. 4.

In FIG. 4 the reference numeral 10 schematically indicates the buried pipeline, 11 the disperser, 12 the reference electrode, 13 the cathodic protection current generator, and 14 the square wave generator.

Contact is produced by striking the pipeline under sliding contact conditions with an excavator bucket which is also in direct contact with the ground, to produce surface damage of some square centimeters.

The table shows the measured values, where R indicates the pipe resistance and RI the ohmic loss between the pipeline and earth, both values relating to one square meter of surface.

TABLE 1

| Defect area/ pipe ratio | Before contact R(ohm) | Before contact RI(mv) | During contact R(ohm) | During contact RI(mv) | After contact R(ohm) | After contact RI(mv) |
|---|---|---|---|---|---|---|
| $10^{-3}$ | 1600 | 2400 | 530 | 795 | 800 | 1200 |
| $10^{-4}$ | 4410 | 6610 | 680 | 1000 | 1170 | 1755 |
| $10^{-5}$ | 11750 | 17625 | 750 | 1125 | 1410 | 2115 |
| $10^{-6}$ | 20890 | 31335 | 775 | 1165 | 1490 | 2235 |
| no defect | $10^9$ | off scale | 800 | 1200 | 1600 | 2400 |

The increase in ohmic loss at the moment of separation between the bucket and pipeline was found in all test cases to be sufficient to trigger the alarm device.

The method and device of the invention are not activated by variations in the insulation or resistance of the covering caused by corrosion or other progressive degradation phenomena deriving from the environment, but are sensitive only to sudden contact with metal bodies, such as contact with power machines. Even sudden variations in the feed voltage to the electrical generators of the cathodic protection system, due for example to mains voltage instability, are unable to interfere with the alarm device according to the invention because of the very high capacity of the pipeline/ground interface, which transforms such events into very slow potential variations.

The overall measurement and alarm system is suitable for remote transmission and unmanned monitoring of a pipeline system distributed over a territory.

We claim:

1. A method for monitoring accidental damage of a protective covering on underground or immersed metal structures subjected to cathodic protection, comprising:
   a) applying and measuring a modulated cathodic protection current;
   b) measuring a variation in potential due to an ohmic loss induced in the structure by said applied current;
   c) determining the electrical resistance of the protective covering by the relationship $R = \Delta V^*/I^*$, wherein R represents the electrical resistance of the protective covering, $\Delta V^*$ represents said induced ohmic loss, and $I^*$ represents said applied current,
   whereby the damage of the protective covering is indicated by a decrease followed by an increase in the value $RI^*$.

2. The method of claim 1, further comprising activating an alarm when the value of $RI^*$ reaches a predetermined value.

3. The method of claim 2, wherein said applied current is permanently modulated and the protective covering is continuously monitored.

4. The method of claim 3, wherein said applied current is symmetrically modulated and comprises square waves having a modulation level below about 10%.

5. The method of claim 3, wherein said square waves are modulated between about 0.5% and about 5.0%.

6. The method of claim 5, further comprising sampling said square waves.

7. A device for monitoring accidental damage of a protective covering on underground or immersed structures subjected to cathodic protection comprising a circuit for sampling a square wave signal, wherein the circuit comprises:
   a) a generator for applying a modulated cathodic protection current, wherein said current comprises square waves;
   b) a voltage/current converter for generating a converted signal from said square wave current;
   c) a differentiator/rectifier for differentiating said converted signal, for generating positive and negative pulses at the wavefronts of said converted signal, and for eliminating said negative pulses and allowing said positive pulses to pass for thereby generating a synchronizing signal;
   d) a monostable multivibrator controlled by said synchronizing signal and for generating a synchronized square wave signal;
   e) a reference electrode inserted in the ground and an electronic switch connected thereto, wherein said electronic switch is adapted for allowing a voltage signal to pass therethrough at the peaks of said synchronized square wave signal, wherein said voltage signal is taken between said reference electrode and said electronic switch, and wherein said electronic switch generates an output signal when damage of the protective covering occurs.

8. The device of claim 7, further comprising a sensor for sensing an increase or decrease in the electrical resistance of the protective covering, comprising:
   a) a peak voltmeter for measuring a peak voltage value;
   b) a low-pass electronic filter for averaging said peak voltage value, for eliminating steep wavefronts in said peak voltage value corresponding to said synchronizing signal, and for generating a low pass signal;

c) a differentiator for determining an increase in ohmic resistance of the protective covering from said low-pass signal and for generating a differentiated signal; and d) an alarm and a blocked Schmitt trigger connected thereto, wherein said trigger is activated by a variation in said differentiated signal and thereby activates said alarm for indicating damage to the protective covering.

* * * * *